(12) United States Patent
Dirauf et al.

(10) Patent No.: US 9,943,271 B2
(45) Date of Patent: Apr. 17, 2018

(54) METHOD AND CONTROL SYSTEM FOR CONTROLLING A MEDICAL DEVICE

(71) Applicant: Siemens Aktiengesellschaft, Munich (DE)

(72) Inventors: Franz Dirauf, Ebensfeld (DE); Thilo Hannemann, Erlangen (DE); Anja Jaeger, Fuerth (DE); Robert Kagermeier, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 174 days.

(21) Appl. No.: 14/731,851

(22) Filed: Jun. 5, 2015

(65) Prior Publication Data

US 2015/0351709 A1 Dec. 10, 2015

(30) Foreign Application Priority Data

Jun. 6, 2014 (DE) .................. 10 2014 210 938

(51) Int. Cl.
*A61B 6/08* (2006.01)
*A61B 6/04* (2006.01)
(Continued)

(52) U.S. Cl.
CPC ............ *A61B 6/0492* (2013.01); *A61B 6/545* (2013.01); *A61B 6/547* (2013.01); *G01B 11/25* (2013.01);
(Continued)

(58) Field of Classification Search
CPC ....... A61B 6/04; A61B 6/0407; A61B 6/0457; A61B 6/0464; A61B 6/0471; A61B 6/0478; A61B 6/0485; A61B 6/0492; A61B 6/54; A61B 6/541; A61B 6/542; A61B 6/545; A61B 6/547; A61B 6/548
USPC ......................... 378/204, 205, 206, 207, 208
See application file for complete search history.

(56) References Cited

U.S. PATENT DOCUMENTS

| 4,256,966 A | * | 3/1981 | Heinz ................ A61B 6/08 250/491.1 |
| 5,539,798 A | | 7/1996 | Asahina et al. |

(Continued)

FOREIGN PATENT DOCUMENTS

| DE | 10 2010 017 857 A1 | 10/2011 |
| DE | 10 2012 205 549 A1 | 10/2013 |

(Continued)

*Primary Examiner* — Jason McCormack
(74) *Attorney, Agent, or Firm* — Schiff Hardin LLP

(57) ABSTRACT

A medical device is controlled as a function of a position of a control element projected onto a projection surface, wherein a geometric property of the projected control element is adjusted to the surface structure. The adjustment is accomplished by means of a transformation of projection data, the projection data corresponding to the control element that is to be projected. The optical projection of the control element is based on the transformed projection data. Such an adjustment and transformation are made possible by determining the surface structure of the projection surface. The control system has an image processor both for determining the surface structure and for transforming the projection data. The control system additionally has a projector for optically projecting the control element and a control unit for controlling the medical device based on the first position of the projected control element.

14 Claims, 4 Drawing Sheets

(51) Int. Cl.
*A61B 6/00* (2006.01)
*G06K 9/00* (2006.01)
*G01B 11/25* (2006.01)
*H04N 9/31* (2006.01)
*A61B 6/03* (2006.01)

(52) U.S. Cl.
CPC ....... *G06K 9/00355* (2013.01); *H04N 9/3185* (2013.01); *A61B 6/032* (2013.01); *A61B 6/4441* (2013.01)

(56) References Cited

U.S. PATENT DOCUMENTS

| | | |
|---|---|---|
| 2005/0013410 A1 | 1/2005 | Hornegger |
| 2005/0058256 A1 | 3/2005 | Beimler et al. |
| 2011/0135190 A1* | 6/2011 | Maad .................. A61B 6/0407 382/154 |
| 2012/0229383 A1 | 9/2012 | Hamilton et al. |
| 2013/0289796 A1* | 10/2013 | Bergfjord ............. A61N 5/1048 700/302 |
| 2014/0114113 A1* | 4/2014 | Matteo .................. G03B 21/14 600/1 |
| 2015/0381905 A1* | 12/2015 | Berman ................ H04N 5/272 396/2 |
| 2015/0381908 A1* | 12/2015 | De Bruijn ............ G01J 5/0896 348/253 |

FOREIGN PATENT DOCUMENTS

| | | |
|---|---|---|
| DE | 10 2012 213 426 A1 | 2/2014 |
| DE | 102014207127 A1 | 10/2015 |

* cited by examiner

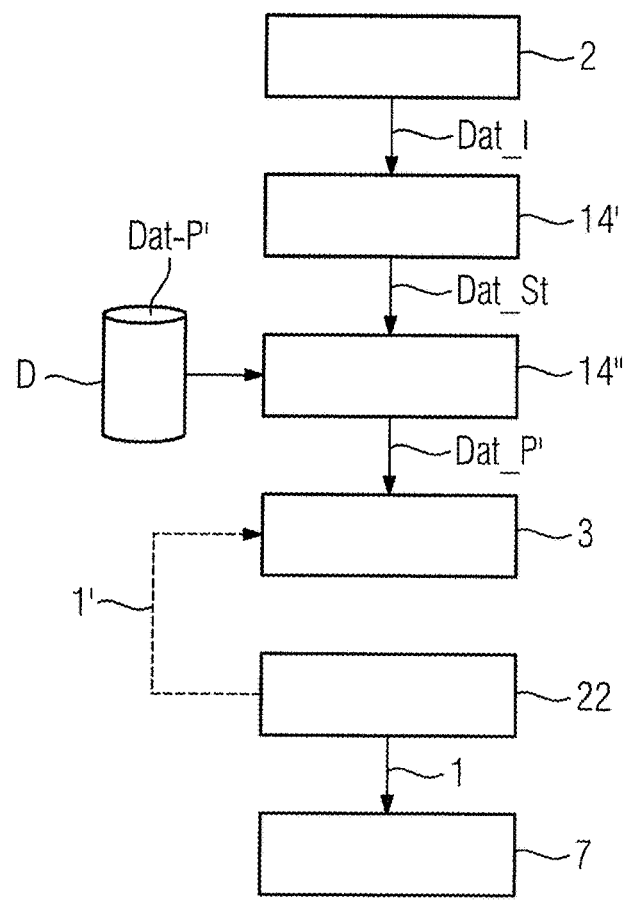
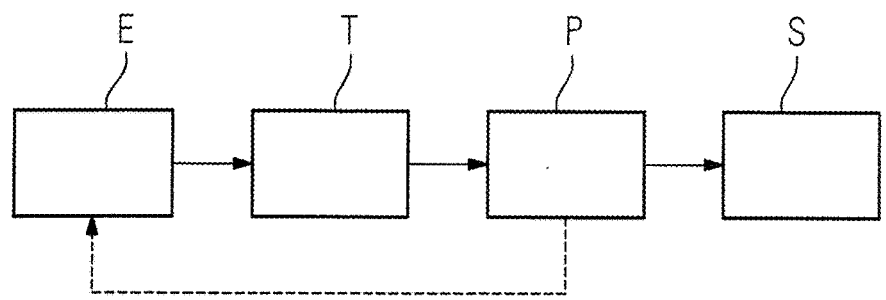

METHOD AND CONTROL SYSTEM FOR CONTROLLING A MEDICAL DEVICE

BACKGROUND OF THE INVENTION

Field of the Invention

The present invention relates to a method and control system for controlling a medical device, and in particular to such a method and system wherein a control element for controlling or operating the medical device is projected onto a surface.

Description of the Prior Art

Modern medical devices have a number of functions in which individual units of the medical device are controlled. Examples of medical devices are a computed tomography device and a C-arm X-ray device. The functions include, for example, the acquisition of measurement data by means of X-ray radiation or the positioning of a C-arm. Furthermore, the control of a medical device can involve the positioning of a patient, for example by moving a patient bed. It is therefore desirable to position the patient as quickly and precisely as possible in accordance with the requirements of a specific protocol or a specific medical problem.

Conventional control elements such as pushbuttons, switches or levers are used for controlling the units of a medical device. With conventional control concepts, however, the control elements are spatially separated from the place at which an interaction is to occur between the medical device and the patient. Optical projections therefore can be used to indicate an interaction zone of the medical device with the patient. Thus, the positioning of the patient in computed tomography is facilitated by the use of laser light, wherein a laser projects a line onto the patient bed or, as the case may be, the patient. LAP Laser and Laser Components are examples of companies manufacturing corresponding lasers. However, the use of optical projections for controlling a medical device is complicated due to the fact that the optical projections are frequently distorted. For this reason, only vertical optical projections of dots or lines have been used in the prior art for the purpose of facilitating the control of a medical device.

SUMMARY OF THE INVENTION

An object of the present invention to facilitate the quick and precise control of a medical device with little susceptibility to error.

The achievement of the object both in relation to the inventive device and the invented method is described below. Features, advantages or alternative embodiment variants cited in this regard are applicable to the other subject matters, and vice versa. The functional features of the method are implemented by corresponding device-related modules.

A basis of the invention is to control a medical device as a function of a first position of a control element projected onto a projection surface, wherein a geometric property of the projected control element is adjusted to the surface structure of the projection surface. The adjustment is accomplished by a transformation of projection data, the projection data corresponding to the control element that is to be projected. According to the invention, the optical projection of the control element is based on the transformed projection data. Such an adjustment and transformation are made possible by determining the surface structure of the projection surface.

The control system according to the invention has an image processor both for determining the surface structure and for transforming the projection data. The control system additionally has a projector for optically projecting the control element and a control unit for controlling the medical device based on the first position of the projected control element.

The invention accordingly makes it possible for the projected control element to have specific geometric properties which facilitate an identification of the control element. This applies both to an automatic and to a user-side identification of the projected control element. In particular, a distortion of the control element due to an uneven projection surface can be avoided or at least reduced. Since a transformation of projection data takes place very quickly, the control element can be adjusted particularly quickly and flexibly to the respective surface structure. The invention consequently results in a quick and precise control of the medical device with little susceptibility to error.

According to a further embodiment of the invention, the transformation can be performed such that the geometric property of the control element is adjusted to an acquisition angle, in particular for the acquisition of the optical projection of the control element. This enables more reliable identification of the control element. In addition, such an adjustment permits specific geometric properties such as an angle or the orientation of a geometric element at an acquisition angle to exhibit a low degree of distortion. The invention thereby produces quick and reliable control.

According to a further embodiment of the invention, the projected control element appears in a predefinable shape at the acquisition angle. This makes it particularly easy to identify the projected control element and to realize precise control of the medical device.

According to a further embodiment of the invention, the surface structure of the projection surface is determined by means of at least one image, in particular a 3D image, of the projection surface. In this case the image can be acquired in particular by means of a 3D camera. This enables the surface structure to be determined precisely and quickly. Accordingly, the transformation with the adjustment of the geometric property and finally the control of the medical device can also be carried out precisely and quickly.

According to a further embodiment of the invention, the at least one image comprises an acquisition of an optically projected stripe or dot pattern onto the projection surface. This enables the distortions of such a pattern that are caused by the projection surface to be used as a basis for determining the surface structure of the latter particularly easily and reliably.

According to a further embodiment of the invention, the image comprises an acquisition of an optical projection of the control element onto the projection surface based on the projection data. This enables the geometric properties of the projected control element to be identified in the acquired image. Because the projection data corresponding to the projected control element is known, the data can now be transformed in a particularly simple manner such that the geometric properties of the control element that is to be projected afresh are adjusted to the surface structure. In other words, this embodiment of the invention enables a feedback process whereby an already completed projection of the control element is used for the transformation of the projection data and consequently for an adjustment of future projections of the control element.

According to a further embodiment of the invention, the medical device is controlled as a function of the first position of the projected control element relative to an input element. The input element can be a hand or a pointer, for example. The first position relative to an input element can be determined for example by means of a camera. According to this embodiment, the invention is designed for controlling the medical device by means of gestures. The control function is implemented in a particularly hygienic manner as a result.

According to a further embodiment of the invention, the control element is projected onto a patient couch or onto a patient positioned on the patient couch, in which case the control element indicates an interaction zone of the medical device with the patient. This concerns a particularly important application of the invention. This is because it is specifically the control of an interaction zone that is particularly important for the safety of the patient. Thus, in the case of X-ray imaging for example, it is critical to ensure that the patient is not exposed to more X-ray radiation than prescribed. As a result, this aspect of the invention solves both the problem of quick and precise control and control with the minimum possible susceptibility to error for a particularly important application case.

The control system according to the invention may also include a patient bed. In particular, the control of the interaction zone can be accomplished by controlling the position of the patient bed.

The invention also encompasses a medical device having a control system according to the invention.

BRIEF DESCRIPTION OF THE DRAWINGS

FIG. 2 is a block diagram of a control system for a medical device.

FIG. 3 is a flowchart for controlling a medical device in accordance with the invention.

DESCRIPTION OF THE PREFERRED EMBODIMENTS

Figure 1:
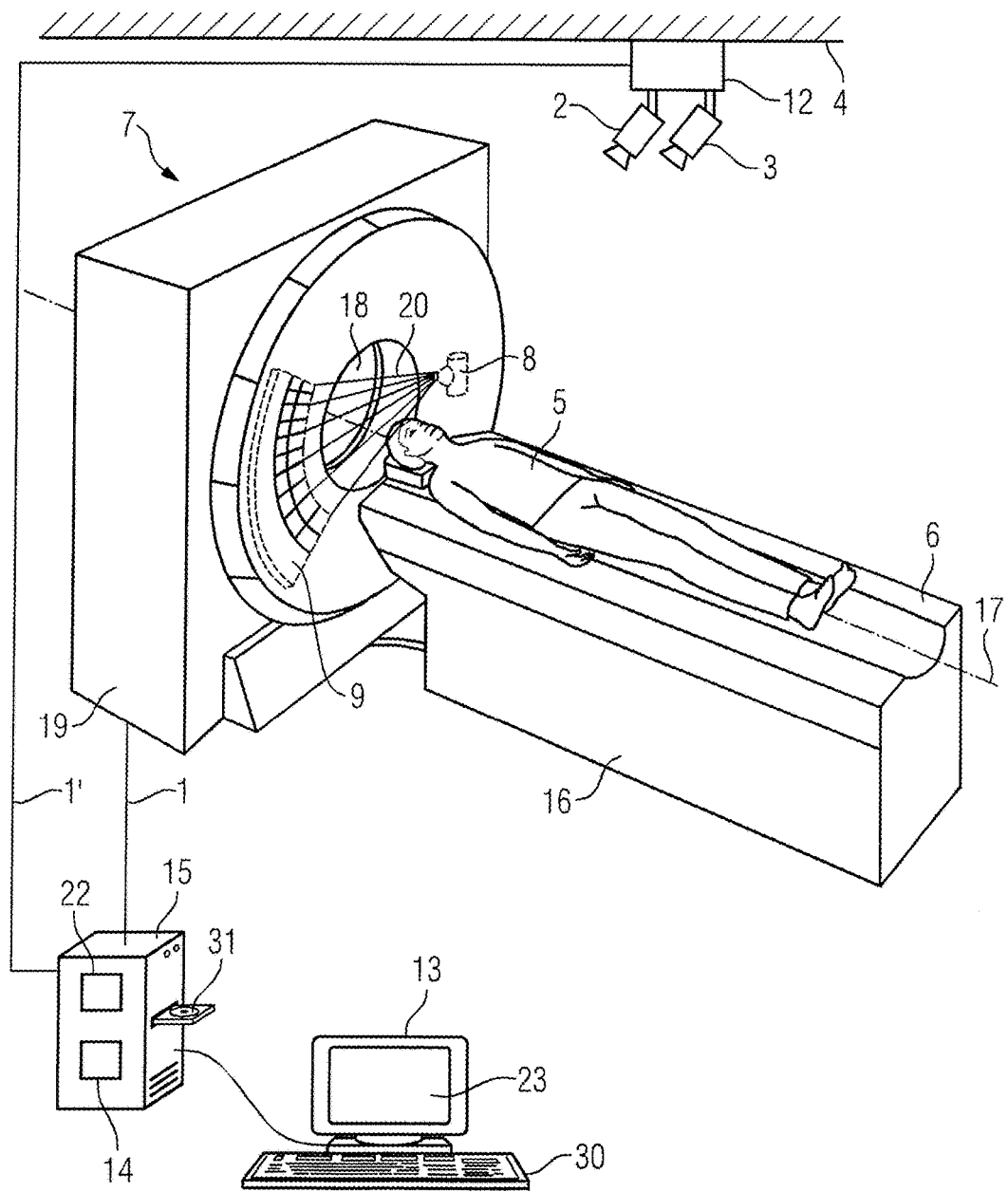
FIG. 1 shows a control system for a medical device, using a computed tomography system as an example.

FIG. 1 shows a control system for a medical device. A medical device 7 is an at least partially electronically controllable device which serves for medical purposes. In particular, a medical device 7 can facilitate a diagnosis or treatment. Thus, the medical device 7 may be a system for irradiating a patient 5 with high-energy radiation such as electrons or ions, for example. It may also be an imaging medical device for acquiring images of a patient 5, in particular for acquiring images of an interaction zone 28. The interaction zone 28 can in this case cover specific organs or parts of the body, for example the abdomen or heart of a patient 5. Such an acquisition is performed for example by radiofrequency electromagnetic radiation, in particular X-ray radiation, emitted at high frequencies compared to visible light. During the acquisition of an image, the patient 5 lies on a patient bed 6 which is coupled to a couch base 16 such that the latter carries the patient bed 6 together with the patient 5. Furthermore, an imaging medical device can be configured to acquire a tomographic image of a patient 5.

The acquisition of a tomographic image entails a spatially three-dimensional scanning of the patient 5 positioned on the patient bed 6. Such a scan can be effected in particular by means of a relative movement of patient 5 and an image acquisition unit.

In the example shown here, the patient bed 6 is moved during an acquisition of a tomographic image along a system axis 17 through the aperture 18 of the gantry 19 of a computed tomography system. In the course of said movement, a plurality of X-ray projections of an interaction zone 28 are acquired. Spatially three-dimensional X-ray images, in particular cross-sectional images or slices, can be reconstructed from said X-ray projections. During the tomographic acquisition of an X-ray image, the image acquisition unit, in the case shown here, rotates together with an X-ray detector 9 and an X-ray emitter 8, which cooperatively interacts with the X-ray detector 9, around the system axis 17. X-ray emitter 8 and X-ray detector 9 are arranged in a gantry 19 in so that they are aligned opposite each other and the X-ray beams of the X-ray emitter 8 can be detected by the X-ray detector 9. In the example shown here, the X-ray emitter 8 is an X-ray tube and the X-ray detector 9 is a detector having a plurality of rows and columns.

In an alternative embodiment variant (not shown), the medical device 7 is a C-arm X-ray device. In a C-arm X-ray device, in particular different types of X-ray emitters 8 and X-ray detectors 9 can be used. For example, a flat-panel detector can be used as X-ray detector 9. In other embodiment variants, the medical device 7 is a magnetic resonance tomography scanner in which a magnet is used for generating radiation and a coil is used for detecting radiation.

The control system according to the invention additionally comprises a projector 3. An optical projection is a projection of the light generated by the projector 3. A projector 3 is configured for generating light, i.e. electromagnetic radiation in the visible spectral range. For example, the projector 3 can generate light by a filament lamp, a halogen lamp, a diode or a laser. In this case the projector 3 can be embodied as a scanner which generates a planar projection by high-speed sampling ("scanning") of the projection surface by means of a light spot or a light line. High-speed, in this context, means that the scanning process is imperceptible to the human eye. The projector 3 can, however, also generate a static projection without a scanning process. In addition, a projector 3 typically has optical elements such as lenses for generating the projection. The projector 3 is functionally connected to a signal processing unit for generating a projection in accordance with a control signal 1'. The signal processing unit can be embodied in the form of both hardware and software.

A projection, within the meaning of the present application, can be embodied both in planar form, and as lines and dots. A projection is planar when it appears planar to the human eye. A projection requires a projection surface from which the light emitted by the projector 3 is refracted and/or reflected. A projection can be made on an even projection surface or also on a projection surface which has a curved surface in three-dimensional space. In particular, the surfaces of the projection surface may be curved in a non-uniform manner. Thus, the patient bed 6 and/or the surface of the patient 5 are/is generally not structured evenly, but are/is curved and irregular in structure. The projection surface may also be composed of several partial surfaces.

A control element 10, within the meaning of the present application, is a clearly recognizable part of a projection which in particular can have clearly identifiable contours and be embodied as a geometric figure. For example, the schematic control element 10 can be embodied in the shape of a rectangle, an ellipse or a line. Furthermore, a control element 10 can be contrasted in terms of color or distinguished from other parts of the projection on account of its brightness. The control element 10 can be projected as a function of a predefined workflow or as a function of an examination protocol, in particular for the acquisition of a tomographic image. For example, specific control steps are necessary at a specific time instant of a workflow. Those control elements 10 that are configured for initiating a control step and/or defining a parameter of the respective control step are then projected at the time instant.

An input element 11 is a material object that has a suitable size and suitable optical properties in order to be able to be identified in an image acquired by means of a camera 2. In particular, the input element 11 can be a bodily object such as a finger, a hand or a foot. Furthermore, an input element 11 can also be an object that is highlighted in terms of its color and/or geometrically, for example a fluorescent object or a stick-shaped object.

The camera 2 is a camera for recording images. The camera 2 is configured for detecting electromagnetic radiation, in particular for detecting electromagnetic radiation in a low-frequency spectral range by comparison with X-ray radiation, in the visible or infrared spectral range, for example. If the camera 2 is configured to acquire images directly with spatial depth information, it is also referred to as a 3D camera. The camera 2 is embodied for example as a stereo camera or as a transit-time measurement system (also known as a "time-of-flight camera"). In a further embodiment of the invention, the camera 2 is configured by means of structured illumination for recording images with spatial depth information. For this reason the control system may also have an illumination unit for generating a stripe pattern on the projection surface.

A 3D image contains spatially three-dimensional information. In particular, a 3D image can be produced by means of a conventional 2D image and a dataset relating to depth information corresponding to the 2D image. A 2D image contains spatially two-dimensional information. The information of the 2D image or 3D image has been acquired by means of optical methods and can be visualized, in particular in the form of picture elements such as pixels or voxels. In particular, each pixel in the 2D image can be assigned corresponding depth information. The resolution of the 2D image may be different from the resolution of the depth information, however. Furthermore, the depth information can relate to the surface contours of an object imaged in the 2D image, in particular to the surface structure of a projection surface.

In the example shown in FIG. 1, both the projector 3 and the camera 2 are mounted by means of a retaining fixture 12 to the ceiling 4 of a room. In other embodiment variants, both the projector 3 and the camera 2 can be mounted on the wall of a room or on a separate frame or on the medical device 7 itself. Advantageously, the projector 3 is positioned and secured in such a way that the geometric distortions of the projection are minimized. In particular, the projector 3 can be mounted centrally above the patient bed 6. Centrally, in this context, means that the projector 3 is located midway over the patient bed 6 with respect to both the longitudinal and the transverse axis.

The control system can furthermore be connected to a computer 15 or can incorporate a computer. In the embodiment variant shown here, the computer 15 has further interfaces in order to be able to communicate with the output unit 13. The interfaces are generally known hardware or software interfaces, e.g. the hardware interfaces PCI bus, USB or Firewire. The computer 15 is connected to an output unit 13, for example to allow the graphical output 23 of images of the projection surface or, as the case may be, of the interaction zone 28. The output unit 13 is for example one (or more) LCD, plasma or OLED screen(s). The computer 15 can also be connected to an additional input unit 30.

The control system can have a control unit 22 that is configured for controlling the medical device 7. In developments of the invention, the control unit 22 is configured for controlling further units of the control system, such as the projector 3 for example. The control system may also have further control units for controlling individual units of the control system. The control unit 22 has components in the form of hardware or software for calculating at least one control signal 1. The control signal from the control unit 22 to the unit that is to be controlled at a given time can be transmitted either by means of a fixed cable connection or wirelessly.

The control system according to the invention additionally has an image processor 14 that can be designed in the form of both hardware and software. The image processing unit 14 is configured for determining the surface structure of the projection surface based on at least one image recorded by the camera 2. In a further embodiment of the invention, the image processing unit 14 is configured for determining an input element 11 in an image acquired by the camera 2 as well as for determining a position of the input element 11 relative to the control element 10. In an embodiment of the invention, the image processor 14 is configured for communicating with the control unit 22, in particular in order to signal to the control unit 22 the position of the input element 11 relative to the control element 10.

The computer 15 is configured to load a computer program into its internal memory, the computer program comprising commands that can be read by the computer 15. The commands of the computer program that are readable by the computer 15 are configured to control the method according to the invention when the commands are executed on the computer 15. In further embodiment variants of the invention, both the computer program and a control unit 22 are configured to access images recorded by the camera 2 or information obtained from the images and to generate a control signal 1 for controlling the projector 3 and the projection process. The computer program can furthermore be stored on a computer-readable medium 31. The computer-readable medium 31 can also be a DVD, a USB stick, a hard disk or a floppy disk, for example.

FIG. 2 shows a schematic layout of a control system for a medical device. In this case a camera 2 is used for recording an image of a projection surface. In the exemplary embodiment shown here, the image data Dat_I, which corresponds to the image of the projection surface, is transmitted by the camera 2 to a first image processing unit 14'. The latter determines the surface structure of the projection zone and generates structure data Dat_St, which corresponds to the surface structure of the projection surface. Projection data Dat_P is also stored on a storage medium D. The structure data Dat_I is used in order to transform projection data Dat_P into transformed projection data Dat_P'. The transformation is effected by means of a second image processing unit 14". The projector 3 generates an optical projection of the control element 10 onto the projection surface based on the transformed projection data Dat_P'.

The control unit 22 generates a control signal 1 for controlling the medical device 7 as a function of a first position of the projected control element 10. This functional dependence consists for example in that an image of the now projected control element 10 acquired by the camera 2 serves for control purposes. For example, such an image can be sent directly to the control unit 22 and be evaluated by the latter. In a further embodiment variant, the image is evaluated by the image processing unit 14' or 14" and the result of the evaluation is sent for control purposes to the control unit. The result can relate to the recognition of a gesture in an image or to the relative position of input element 11 and control element 10.

FIG. 3 shows a flowchart for controlling a medical device. In an optical projection of a control element 10, distortions can occur as a function of the projection angle as well as of the surface structure of the projection surface. Such distortions are problematic in particular when the projected control element 10 is to be used for controlling a medical device 7, because the control function is rendered susceptible to error thereby. If an interpretation of the distortedly projected control element 10 by a user is necessary for control purposes, the control function is also made slower due to the distortion. The present invention allows such distortions to be corrected so that the control of a medical device 7 based on a projected control element can be performed more quickly and more reliably. To that end the following steps are implemented according to the invention:

determination E of a surface structure of a projection surface, transformation T of projection data, wherein the projection data corresponds to (represent) a control element 10 that is to be projected, wherein a geometric property of the control element 10 that is to be projected is adjusted (matched) to the surface structure, optical projection P of the control element 10 onto the projection surface based on the transformed projection data, control S of the medical device 7 as a function of a first position of the projected control element 10.

Figure 4:
FIG. 4 shows an image of a projection of a stripe pattern.

The surface structure can be determined in a manner that is generally known, for example based on an image, recorded by means of a camera 2, of a stripe pattern projected onto the projection surface. In this case the projection data corresponding to the stripe pattern are known, as is also the projection angle for projecting the stripe pattern. Geometric properties of the stripes relative to one another in the image acquired by the camera 2 can then be evaluated. The properties of the stripes relative to one another relate for example to the orientation and/or the angles of the stripes relative to one another and/or to their width. FIG. 4 shows, as an example, the image of a projection of a stripe pattern onto an uneven projection surface. The surface structure can also be determined directly by the acquisition of a 3D image by means of a 3D camera.

The goal of the determination E of the surface structure is to enable an optical projection P of the control element 10, based on the transformed projection data, such that the projected control element 10 appears less distorted than would be the case without the transformation T. In particular, the transformation T can be performed so that the geometric property is adjusted with respect to an acquisition angle. The acquisition angle can correspond, for example, to the acquisition angle of a camera or to the position of an observer. Furthermore, the transformation can be performed so that, at the acquisition angle, the control element 10 has specific geometric properties such as specific lengths, angles, or a specific shape.

The transformation T can be based on a mathematical mapping between two image spaces which can be realized in particular by the mapping between grid points. The projection data of one grid structure is then mapped onto a grid structure corresponding to the surface structure of the projection surface. The transformed image data can be calculated from such a mapping rule, in particular taking into account a predefined acquisition angle and/or other boundary conditions. The transformation can be performed with pixel-level precision, i.e. so that after the transformation, each original grid point of the projection data is assigned at least one transformed value. Furthermore, the transformation can be performed by interpolation, in particular by an interpolation in the mathematical mapping between two image spaces.

The projection data can relate to different values, such as brightness values and color values. Both brightness values and color values thus can be transformed. In one embodiment of the invention, the determination E of the surface structure also includes determining color information of the projection surface. It is thereby possible during the transformation T to adjust not only a geometric property, but also a color property of the control element 10 that is to be projected to the color information of the surface structure. The transformation T is then performed so that the projected control element 10 produces a predefined color impression. The color values are then present, for example, according to the hue scale or the RGB scale, and can also be transformed according to such scales.

As indicated by a dashed line in FIG. 3, the following steps can also be carried out recursively:—determination E,—transformation T,—optical projection P. In one embodiment variant of the invention, these steps are performed recursively until such time as an abort criterion is reached. The abort criterion is given, for example, by the fact that the transformation T between two succeeding recursion loops is different by not less than a limit value. This enables a dynamic correction which is advantageous for example if the patient 5 onto whom the control element 10 is projected moves.

A dynamic correction can also be useful if there is a change in the acquisition angle. In one embodiment variant of the invention, the camera 2 is worn by the user. For example, the camera 2 is attached to glasses or to another device that is wearable on the head of the user. The transformation T can then adjust the control element 10 that is to be projected to the acquisition angle 2 and consequently to the line of sight of the user. The superimposed control element 10 then appears to the user in the same shape even in the event of a movement of the head. The control S of the medical device 7 is carried out in an even more reliable manner as a result.

Finally, the control S of the medical device 7 is carried out as a function of a first position of the projected control element 10. In a further embodiment variant of the invention, the control step is part of a recursive method. As a result, the dynamic correction also extends to the case where the patient 5 onto whom the control element 10 is projected is moved as a result of a step of the control S.

Figure 5:
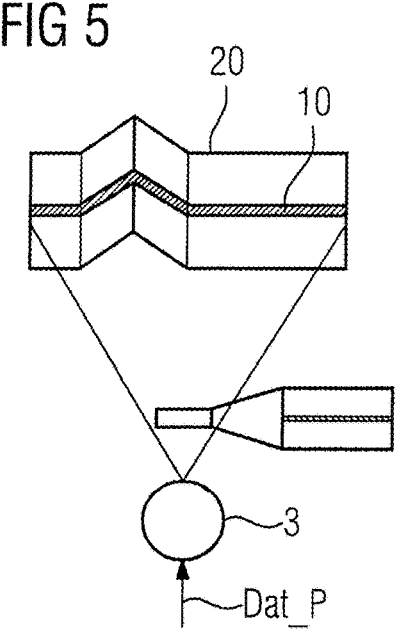
FIG. 5 shows an optical projection without correction.
Figure 6:
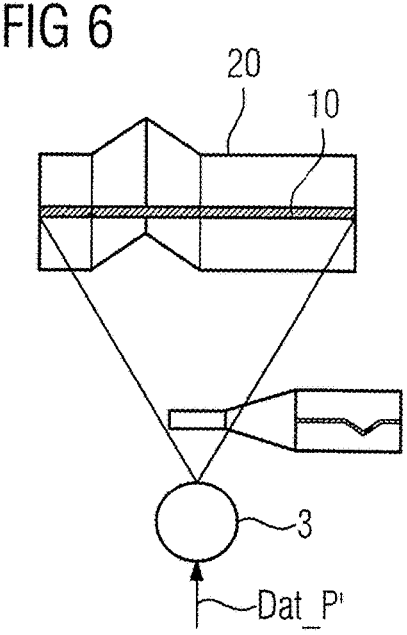
FIG. 6 shows an optical projection with correction.

FIG. 5 and FIG. 6 illustrate the effect of a correction by transformation of the projection data. If an optical projection of a control element 10 is made onto an uneven projection surface 20, the projected control element 10 can appear distorted as in the example shown in FIG. 5. The non-transformed projection data Dat_P correspond to a straight line, but due to the surface structure of the projection surface 20, this appears to have a kink at the acquisition angle chosen here. In FIG. 6, the optical projection is made based on the transformed projection data Dat_P', which correspond to a line with a kink. At the chosen acquisition angle, however, the projected control element 10 appears, as desired, as a straight line, i.e. the distortion is rectified.

Figure 7:
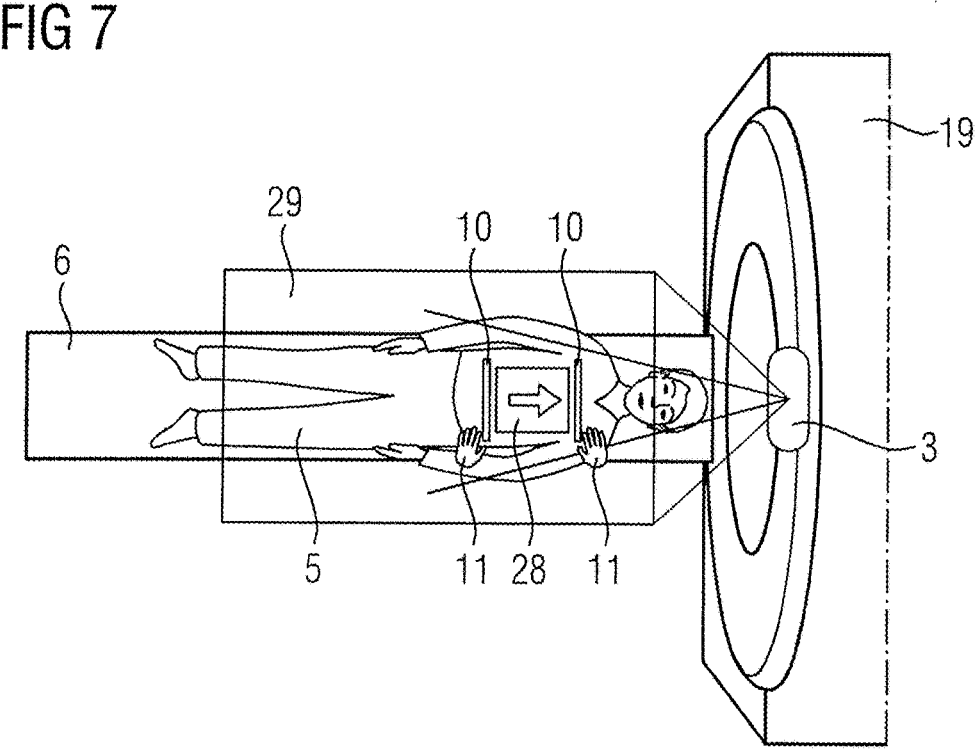
FIG. 7 shows an optical projection of a control element.

FIG. 7 shows an example of an optical projection of a control element. The patient 5 lies on a patient bed 6. The projection zone 29 available for the projector 3 in the embodiment variant shown is characterized by a rectangle. The projection surface that is actually used for the optical projection is located within the projection zone 29. In the example shown here, the projector 3 projects control elements 10 in the form of demarcation lines which delimit the interaction zone 28. Also depicted here are the input elements 11 in the form of hands of a user. By recording images containing the control elements 10 and the input element 11 by means of a camera 2 it is possible to determine at least one first position of a projected control element 10 relative to an input element 11. The control unit now permits the interaction zone 28 to be controlled based on said first position relative to an input element 11, i.e. in particular relative to the hands of the user.

For example, the control element 10 is projected in the form of a narrow stripe along the system axis 17, in particular onto an edge section of the patient bed 6. The control element 10 then indicates the extent of the interaction zone 28 along the system axis 17. Alternatively, the control element 10 can be projected onto the patient bed 6 or onto a patient 5 positioned on the patient bed 6 such that it indicates the extent of the interaction zone 28 both along the system axis 17 and also perpendicularly thereto. The extent of the interaction zone 28 can then be controlled in two dimensions by a corresponding positioning and/or movement of the input elements 11.

It can be ensured by an appropriate calibration that the relationship between the external coordinate system, in which the acquisition region 26 is located, and the internal coordinate system of the projector 3 (and a projection) as well as the camera 2 (and an image) is known to the control system. The control signal 1' effects an optical projection in such a way that the projection appears at a predefined position in the external coordinate system. In this way the location of the control element 10 at any given time is known to the image processing unit 14. The image processor 14 or another unit of the control system is therefore configured to convert the position in an image, in particular in a 3D image, into a position in the external coordinate system by means of a coordinate transformation.

The position of the projected control element 10 and/or of an input element 11 in an image can be determined with the aid of segmentation and/or pattern recognition. The image processing unit can thus determine a position of the projected control element 10 and/or of an input element 11, and moreover both in relation to the internal coordinate system of an image recorded by the camera 2 and to the external coordinate system. The medical device 7 can be controlled in particular by the triggering of a control step due to the undershooting of a defined distance between the first position of the control element 10 and the input element 11. The undershooting of the defined distance corresponds to the activation of the respective control element 10.

In the embodiment variant shown here, a 3D camera 2 is used to ensure that the distance between input element 11 and control element 10 can be determined with maximum accuracy. An accurate determination of the distance on the basis of the determination of the first position of the control element 10 relative to the input element 11 also enables precise and therefore reliable and safe control of the medical device 7. The position of the input element 11 can be determined differently in different embodiment variants; for example, the position of a defined center or of the edge of the input element 11 can be evaluated. In a further embodiment of the invention, the orientation of the input element 11 can also be evaluated in addition to the position, in particular the position and orientation of individual parts of an input element 11 or of different input elements 11 relative to one another. In this way the recognition of gestures for controlling the medical device 7 is also made possible.

A gesture is a defined sequence of individual movement steps of the input element 11. In particular, a control gesture can be identified on the basis of movement steps of individual parts of the input element 11 or of a plurality of input elements 11 relative to one another. If the input element 11 is a hand, a control gesture can be identified for example by the movement of the whole hand and/or by a movement of individual fingers relative to one another.

Furthermore, it is possible for the change in the position of the input elements 11 relative to the control elements 10 to be determined by multiple acquisition of images. Such a multiple image acquisition permits in particular the projected control element 10 to be adjusted to the changing position of the input elements 11. In the example shown here, a movement of the user's hands along the system axis 17 leads to a displacement of the demarcation lines. A movement of the input elements 11 therefore permits the interaction zone 28 to be modified dynamically. Furthermore, in the example shown here, the projector 3 also projects the interaction zone 28 as well as the direction of an acquisition of an image by means of the medical device 7. The adjustment can also be effected by changing specific properties of the projection of the control element 10. Such properties can relate to the brightness, the contrast or the color of the control element 10. Such a property can change in particular upon activation of the control element 10.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for controlling a medical device, said method comprising:

while a patient is on a patient bed of a medical device, acquiring a 3D surface structure data record representing a surface structure, comprising a curvature, of a non-planar projection surface of at least one of said patient and said patient bed;

providing a computer with a projection data record comprising projection data representing a control element of the medical device that is to be projected on said projection surface, said control element having a geometric property that is represented in said projection data;

also providing said computer with said 3D surface structure data record and, in said computer, automatically transforming said projection data in said projection data record to adjust said geometric property of the control element to said curvature of said surface structure of the non-planar projection surface as represented in said surface structure data record, thereby generating a transformed projection data record;

using said transformed projection data record operate a projector in order to optically project said control element onto said projection surface without distortion of said geometric property of said control element due to said curvature of said surface structure of said non-planar projection surface, thereby optically projecting a non-distorted control element onto said non-planar projection surface with said control element exhibiting a control element position;

controlling said medical device dependent on said control element position of said non-distorted control element projected onto said non-planar projection surface;

operating a camera, having a field of view, to obtain an camera image of said non-planar projection surface with said non-distorted control element projected thereon;

introducing an input element into said field of view of said camera, and thereby also detecting said input element in said camera image;

in said computer, analyzing said camera image to determine a relative position of said input element in said camera image to said non-distorted projection of said control element in said camera image; and controlling said medical device dependent on said relative position of said input element to said non-distorted projection of said control element in said camera image.

2. A method as claimed in claim 1 comprising acquiring said surface structure data record at an acquisition angle, and wherein transforming said projection data record includes adjusting said geometric property with respect to said acquisition angle.

3. A method as claimed in claim 2 comprising adjusting said geometric property relative to said acquisition angle to give said geometric property a predetermined geometric shape in said non-distorted control element projected onto said non-planar projection surface.

4. A method as claimed in claim 1 comprising acquiring said 3D surface structure data record of said non-planar projection surface as a 3D image of said non-planar projection surface.

5. A method as claimed in claim 4 comprising acquiring said 3D image as an optically projected stripe or dot pattern onto said non-planar projection surface.

6. A method as claimed in claim 4 comprising acquiring said 3D image as an optical projection of said control element onto said non-planar projection surface using said projection data in said projection data record, prior to transforming said projection data record.

7. A method as claimed in claim 1 wherein said control element indicates an interaction zone of said medical device with said patient on said patient bed.

8. A control system for a medical device, said control system comprising:

an acquisition unit configured to acquire a 3D surface structure data record, while a patient is on a patient bed of a medical device, representing a surface structure, comprising a curvature, of a non-planar projection surface of at least one of said patient and said patient bed;

a processor configured to receive said 3D surface structure data record and a projection data record comprising projection data representing a control element of the medical device that is to be projected on said non-planar projection surface, said control element having a geometric property that is represented in said projection data;

said processor being configured to automatically transform said projection data in said projection data record to adjust said geometric property of the control element to said curvature of said surface structure of the non-planar projection surface as represented in said surface structure data record, thereby generating a transformed projection data record;

an optical projector in communication with said processor;

said processor being configured to use said transformed projection data record to operate said projector to optically project said control element onto said non-planar projection surface without distortion of said geometric property of said control element due to said curvature of said surface structure of said projection surface, thereby optically projecting a non-distorted control element onto said non-planar projection surface with said control element exhibiting a control element position;

a camera, having a field of view, positioned to obtain a camera image of said non-planar projection surface with said non-distorted control element projected thereon;

an input element introduced into said field of view of said camera, with said input element then also being detected in said camera image;

said computer being configured to analyze said camera image to determine a relative position of said input element in said camera image to said non-distorted projection of said control element in said camera image; and said control computer being configured to control said medical device dependent on said relative position of said input element to said non-distorted projection of said control element in said camera image.

9. A control system as claimed in claim 8 wherein said acquisition unit is configured to acquire said surface structure data record at an acquisition angle, and wherein said processor is configured to transform said projection data record by adjusting said geometric property with respect to said acquisition angle.

10. A control system as claimed in claim 9 wherein said processor is configured to adjust said geometric property relative to said acquisition angle to give said geometric property a predetermined geometric shape in said non-distorted control element projected onto said non-planar projection surface.

11. A control system as claimed in claim 8 wherein said acquisition unit is configured to acquire said 3D surface structure data record of said non-planar projection surface as a 3D image of said non-planar projection surface.

12. A control system as claimed in claim 11 wherein said acquisition unit is configured to acquire said 3D image as an optically projected stripe or dot pattern onto said non-planar projection surface.

13. A control system as claimed in claim 11 wherein said acquisition unit is configured to acquire said 3D image as an optical projection of said control element onto said non-planar projection surface using said projection data in said projection data record, prior to transforming said projection data record.

14. A control system as claimed in claim 8 wherein said control element indicates an interaction zone of said medical device with said patient on said patient bed.

\* \* \* \* \*